(12) United States Patent
Schür

(10) Patent No.: US 7,323,187 B1
(45) Date of Patent: Jan. 29, 2008

(54) IMPREGNATION METHOD

(76) Inventor: Jörg Peter Schür, Heideweg 51, D-41844 Wegberg-Dalheim (DE)

( * ) Notice: Subject to any disclaimer, the term of this patent is extended or adjusted under 35 U.S.C. 154(b) by 0 days.

(21) Appl. No.: 10/070,042

(22) PCT Filed: Aug. 28, 2000

(86) PCT No.: PCT/EP00/08381

§ 371 (c)(1),
(2), (4) Date: Jul. 18, 2002

(87) PCT Pub. No.: WO01/15528

PCT Pub. Date: Mar. 8, 2001

(30) Foreign Application Priority Data

Aug. 27, 1999 (DE) ............................... 199 40 605

(51) Int. Cl.
*A01N 25/32* (2006.01)

(52) U.S. Cl. .................. 424/406; 424/405; 514/557; 514/558; 514/560; 514/566; 514/730; 514/731; 514/738

(58) Field of Classification Search .............. 424/405, 424/406; 514/557, 558, 560, 566, 730, 731, 514/738
See application file for complete search history.

(56) References Cited

U.S. PATENT DOCUMENTS

| | | |
|---|---|---|
| 1,331,331 A | 2/1920 | Erslev |
| 1,790,596 A | 1/1931 | Schneible |
| 2,409,088 A | 10/1946 | Weits |
| 2,496,281 A | 2/1950 | Fisher |
| 2,596,106 A | 5/1952 | Schneible |
| 2,683,074 A | 7/1954 | Kuehner |
| 2,886,297 A | 5/1959 | Crandall |
| 3,191,363 A | 6/1965 | Martin, Jr. |
| 3,363,403 A | 1/1968 | Vicard |
| 3,442,602 A | 5/1969 | Diehl |
| 3,518,096 A | 6/1970 | Layton |
| 3,557,535 A | 1/1971 | Howick |
| 3,788,045 A | 1/1974 | Arnold |
| 3,908,031 A | 9/1975 | Wistreich |
| 3,989,485 A | 11/1976 | Kilian |
| 4,110,430 A | 8/1978 | Hopp |
| 4,200,442 A | 4/1980 | Willot |
| 4,361,554 A | 11/1982 | Saunders |
| 4,446,161 A | 5/1984 | Friedman |
| 4,512,935 A | 4/1985 | Hilmersson |
| 4,544,666 A * | 10/1985 | Thirumalachar et al. .... 514/460 |
| 4,579,569 A | 4/1986 | Sheng |
| 4,602,011 A | 7/1986 | West |
| 4,624,688 A | 11/1986 | Vatunen |
| 4,806,526 A | 2/1989 | Green |
| 4,808,396 A | 2/1989 | Shibanai |
| 4,810,268 A | 3/1989 | Chambers |
| 4,927,651 A | 5/1990 | Kumani |
| 4,977,142 A | 12/1990 | Green |
| 5,030,253 A | 7/1991 | Tokuhiro |
| 5,089,268 A | 2/1992 | Katz |
| 5,091,405 A | 2/1992 | Stevenson |
| 5,143,720 A | 9/1992 | Lopes |
| 5,201,919 A | 4/1993 | Jahn |
| 5,322,689 A | 6/1994 | Hughes et al. |
| 5,362,520 A * | 11/1994 | Rodriguez .................. 427/393 |
| 5,397,385 A * | 3/1995 | Watts ...................... 106/18.32 |
| 5,416,075 A | 5/1995 | Carson et al. |
| 5,439,690 A | 8/1995 | Knight |
| 5,472,684 A | 12/1995 | Nabi |
| 5,474,774 A | 12/1995 | Walker |
| 5,480,519 A | 1/1996 | Abbott |
| 5,480,591 A | 1/1996 | Lagneaux |
| 5,527,552 A | 6/1996 | Todd, Jr. |
| 5,547,540 A | 8/1996 | Ruscheweyh |
| 5,569,461 A | 10/1996 | Andrews |
| 5,661,104 A | 8/1997 | Virgilio |
| 5,665,432 A * | 9/1997 | Kuwazuru et al. .......... 427/325 |
| 5,686,082 A | 11/1997 | N'Guyen |
| 5,695,801 A | 12/1997 | Oh |
| 5,747,416 A | 5/1998 | McArdle |
| 5,750,563 A | 5/1998 | Honda |
| 5,766,314 A | 6/1998 | Weber |
| 5,814,325 A | 9/1998 | Rod |

(Continued)

FOREIGN PATENT DOCUMENTS

| | | |
|---|---|---|
| BE | 515423 | 11/1952 |
| CA | 2012288 | 9/1990 |
| CA | 2 336 565 | 1/2000 |
| CA | 2 355 595 | 5/2000 |
| CA | 2 376 517 | 1/2001 |

(Continued)

OTHER PUBLICATIONS

CAS Tannin Printout RN# 1401-55-4, 2004.*
U.S. Appl. No. 09/743,883, filed Mar. 26, 2001, Jörg Peter Schür.
U.S. Appl. No. 10/019,239, filed May 13, 2002, Jörg Peter Schür.
U.S. Appl. No. 10/019,240, filed May 13, 2002, Jörg Peter Schür.
U.S. Appl. No. 10/069,476, filed Jul. 1, 2002, Jörg Peter Schür.

(Continued)

*Primary Examiner*—Neil S. Levy
(74) *Attorney, Agent, or Firm*—John S. Child, Jr.

(57) ABSTRACT

The invention relates to a method for impregnating, incorporating or surface-treating substances/articles that can be microbially decomposed, contaminated and/or infested with parasites and/or that are perishable. The inventive method comprises the following steps: applying a special antimicrobial/antiparasite composition on the substances/articles or incorporating the antimicrobial/antiparasite composition in the substances. The invention further relates to said special antimicrobial/antiparasite compositions, to their use for impregnating and/or surface-treating substances that can be microbially decomposed, contaminated and/or that are perishable or substances that are infested with parasites and to the use thereof in substances and products that have to be self-contaminating.

18 Claims, No Drawings

U.S. PATENT DOCUMENTS

| | | | |
|---|---|---|---|
| 5,879,683 | A | 3/1999 | Hamilton-Miller |
| 6,004,569 | A | 12/1999 | Bessette |
| 6,007,055 | A | 12/1999 | Schifftner |
| 6,033,705 | A | 3/2000 | Isaacs |
| 6,159,523 | A | 12/2000 | Cain |
| 6,207,290 | B1 * | 3/2001 | Blum et al. .................. 428/540 |
| 6,284,259 | B1 | 9/2001 | Beerse |
| 6,348,187 | B1 | 2/2002 | Pan |
| 6,514,551 | B1 | 2/2003 | Schür |
| 6,608,102 | B1 | 8/2003 | Howell |
| 2002/0014707 | A1 | 2/2002 | Zamany |
| 2002/0176882 | A1 | 11/2002 | Schür |
| 2003/0031588 | A1 | 2/2003 | Schür |
| 2003/0198718 | A1 | 10/2003 | Schür |
| 2004/0076614 | A1 | 4/2004 | Schur |
| 2004/0101459 | A1 | 5/2004 | Schür |
| 2005/0035472 | A1 | 2/2005 | Schur |

FOREIGN PATENT DOCUMENTS

| | | |
|---|---|---|
| CA | 2 378 043 | 1/2001 |
| CA | 2 382 429 | 3/2001 |
| CA | 2 382 740 | 3/2001 |
| CA | 2 450 745 | 12/2002 |
| DE | 2423076 | 5/1974 |
| DE | 31 38288 C2 | 4/1982 |
| DE | A-3409793 | 9/1984 |
| DE | A-3721137 | 1/1989 |
| DE | 3138277 A1 | 4/1992 |
| DE | 19612340 | 11/1996 |
| DE | 19617278 A1 | 11/1997 |
| DE | 19726429 A1 | 12/1998 |
| DE | 19831 288 A1 | 1/2000 |
| DE | 19831306 A | 1/2000 |
| DE | 19831309 A1 | 1/2000 |
| DE | 19931185 A1 | 1/2001 |
| DE | 19940283 A1 | 3/2001 |
| DE | 19940605 A1 | 3/2001 |
| DE | 20100121 U1 | 6/2002 |
| DE | 10100595 A1 | 7/2002 |
| DE | 10128563 | 1/2003 |
| DE | 10141734 A1 | 3/2003 |
| EP | 101083 | 1/1984 |
| EP | 0103787 A2 | 3/1984 |
| EP | A-0311091 | 4/1989 |
| EP | 0345149 A2 | 12/1989 |
| EP | 0557946 A1 | 9/1993 |
| EP | A-0687418 | 12/1995 |
| FR | 1400428 | 1/1965 |
| FR | 2228434 | 12/1974 |
| GB | 172993 | 4/1921 |
| GB | 790075 | 2/1958 |
| GB | 1060447 | 3/1967 |
| GB | 1 465 533 | 2/1977 |
| GB | 1571517 | 7/1980 |
| GB | 2 087 724 | 6/1982 |
| GB | 2 178 837 A | 2/1987 |
| JP | 60226992 | 11/1985 |
| JP | 6-211-1675 | 5/1987 |
| JP | 6-212-6931 | 6/1987 |
| JP | 2180267 A | 7/1990 |
| JP | 6-304-238 | 11/1994 |
| JP | 07304609 * | 11/1995 |
| WO | WO 90/08543 A | 8/1990 |
| WO | WO-A-90/08544 | 8/1990 |
| WO | WO 94/14414 | 7/1994 |
| WO | WO 95/31100 | 11/1995 |
| WO | WO-A-97/19683 | 6/1997 |
| WO | WO 98/21955 A1 | 5/1998 |
| WO | 98/54971 * | 12/1998 |
| WO | WO 98/54971 | 12/1998 |
| WO | WO 98/58540 | 12/1998 |
| WO | WO 00/03612 | 1/2000 |
| WO | WO 96/29895 | 1/2000 |
| WO | WO 00/27192 | 5/2000 |
| WO | WO 01/03746 | 1/2001 |
| WO | WO 01/03747 | 1/2001 |
| WO | WO 01/13727 A1 | 3/2001 |
| WO | WO 01/15528 A1 | 3/2001 |
| WO | WO 02/053978 A1 | 7/2002 |
| WO | WO 02/055114 A1 | 7/2002 |
| WO | WO 02/101299 | 12/2002 |
| WO | WO 02/101299 A1 | 12/2002 |

OTHER PUBLICATIONS

U.S. Appl. No. 10/250,659, filed Jul. 3, 2003, Jörg Peter Schür.
Database WPI,Section CH. Week 199411, Derwent Publications Ltd, London, GB; DW 94-088588 & JP 06038678 (Okubo T), Feb. 15, 1994.
Database WPI, Section CH, Week 199028, Derwent Publications Ltd, London, GB; AN 90-213153 & JP 02142703 (Kurita Water Ind KK) May 31, 1990.
Database WPI, Section CH, Week 198726 Derwent Publications Ltd, London, GB; AN 87-181806 & JP 62111675 (Sanraku Ocean) May 22, 1987.
Database WPI, Section CH, Week 198726 Derwent Publications Ltd, London, GB; AN 87-181806 & JP 62111675 (Sanraku Ocean) May 22, 1987.
Database WPI, Section CH, Week 198946 Derwent Publications Ltd, London, GB; AN 1989-337764, & SE 8 900902 (Thorsell W) May 13, 1989.
Database WPI, Section CH, Week 198728 Derwent Publications Ltd., London, GB; AN 1987-196269 & JP 62126931A (Morinaga Milk Co. Ltd) Jun. 9, 1997.
Database WPI, Section CH, Week 199049 Derwent Publications Ltd., London, GB; AN 1990-361964 & CA 2,012288A (Sterling Drug Inc.) Sep. 16, 1990.
Database WPI, Section CH, Week 197819 Derwent Publications Ltd., London, GB; AN 78-33903 A & JP 53032134A (Katsiraua Fine Goods) Mar. 27, 1978.
Database WPI, Section CH, Week 198621 Derwent Publications Ltd., London, GB; AN 86-136554 & SU 1189454A (Ural Vnipi Khim Promy) Nov. 7, 1985.
Database WPI, Section CH, Week 199251 Derwent Publications Ltd., London GB; AN 1992-420381 & JP 04316506A (Nakano Sumese KK) Nov. 6, 1992.
Japanese Patent Publication No. JP 46028797B, (1971), (cover sheet).
Database WPI, Section CH, Week 199216 Derwent Publications Ltd., London, GB; AW 1992-127230 & JP 04 069308A (Do1 K) Mar. 4, 1992.
Patent Abstracts of Japan vol. 014, No. 453 (C-0764) Sep. 28, 1990 JP 02 180267A (Matsushita Electric Works, Ltd) Jul. 13, 1990.
Chemical Abstracts: vol. 102; 165 387 u (1985), Arora, Rewa, Pandex, GN (HB Technical Inst., Kampur 208 002 India) Biol. Mem. 1984 9(1), 98-104 (Eng.).
Chemical Abstracts: vol. 107; 133021g (1987) Food Preservation Composition, Kummamoto, Toshihiko, JP 61 111675 [87 111 675] May 22, 1987.
Chemical Abstracts: vol. 117; 68848 x (1992), Kutsuwa, Yoshiaki (Asahi Denka Kogyo KK) UP 04 79869 [9279869] Mar. 13, 1992.
Chemical Abstracts: vol. 121; 33789; (1994) Sakai, Isao, JP 0678730 [94 78 730]. Mar. 22, 1999.
Kabara, Jon J. [Hrsg] Cosmetic and Drug Preservation, 1984, S 237-270; 275-297.
The Merck Index, Merck & Co., Inc. (Rahway, NJ, 1976), pp. 1172-1173.
Code of Federal Regulations, 21 C.F.R. § 182/515 ) and § 182.20 (Revised as of Apr. 1, 2001).

Lück, Erich: Chemische Lebensmittelkonservierung, 2. Aufl. 1986, pp. 110-113, 127-138, 213.

Database WPI, Section CH, Week 200300 Derwent Publications, London GB; AN 1976-72203X & BE 841452A (Varga) [May 5, 1976].

Database WPI, Week 199613, Derwent Publications, London GB; AN 1996-124045.

Mendez, B., et al., "Effects of Different Lipid Sources in Total Parenteral Nutrition on Whole Body Protein Kinetics and Tumor Growth", Journal of Parenteral and Enteral Nutrition, American Society for Parenteral and Enteral Nutrition, vol. 16: pp. 545-551 (1992).

Database WPI, Week 198517, Derwent Publications Ltd., London, Great Britain, AN 1985-103098 and JP 60 049747 A (San-Yu Shoji KK), Mar. 19, 1985. Abstract.

* cited by examiner

IMPREGNATION METHOD

This application is a national phase filing of co-pending International Application No. PCT/EP00/08381 filed Aug. 28, 2000, which claims the benefit of that application under 35 U.S.C. § 120 and which also claims the benefit under 35 U.S.C. § 119 of German Application No. 119 40 605.7 filed Aug. 27, 1999.

The present invention relates to a method for the impregnation, incorporation or surface treatment of microbially degradable, contaminatable and/or perishable or parasite-attacked substances/objects, comprising the application of a specific antimicrobial/antiparasitic composition to the substances/objects, or the incorporation of the antimicrobial/antiparasitic composition into the substances, to said specific antimicrobial/antiparasitic compositions, their use for the impregnation or surface treatment of microbiologically degradable, contaminatable and/or perishable or parasite-attacked substances, and their use in substances and products which have to be self-decontaminating.

The impregnation and surface treatment of microbiologically and parasite-sensitive, i.e., contaminatable, degradable and/or perishable substances and objects is a fundamental problem in the industrial processing of such substances and objects (such as wood/timber and wood products, textiles and textile raw materials, and plastics, insulation and sealant materials prone to germ contamination). Also, the self-decontamination of cleaning agents or body care agents, e.g., deodorants, with harmless substances is still decidedly problematic.

Today, a microbiological or parasite attack is controlled exclusively by "toxic" methods, i.e., with bactericidal, fungicidal, virucidal, sporicidal, insecticidal substances, which are highly toxic to a major part thereof, however, so that the persons which come into contact with the thus treated products are endangered. In addition, there are also problems with the disposal of products, substances and objects treated with such toxic substances.

It has been the object of the present invention to provide an impregnation or surface treatment method which is not subject to the disadvantages of the prior art.

Surprisingly, it has now been found that specific antimicrobial compositions which contain two or more GRAS (generally recognized as safe) flavoring agents (such as those known from WO 96/29895 and 98/58540 as processing aids and additives for foodstuffs) also have very good fungicidal and antiparasitic properties. Based on this finding, it was further found that these compositions are very suitable for the impregnation and surface treatment of microbially degradable, contaminatable and/or perishable subjects/objects, and for incorporation into such substances/objects without resulting in the toxicity problem of the conventional impregnation, surface treatment or incorporation agents. By the incorporation, a decontaminating effect of the product (if any) can be enhanced, and thus the toxic substances previously used for this purpose can be replaced. Especially, it was found that the compositions containing benzyl alcohol have particularly high antimicrobial and antiparasitic activities.

Thus, the present application relates to:

(1) a method for the impregnation and treatment of microbially degradable, contaminatable and/or perishable substances or parasite-attacked substances, comprising the distribution or application of an antimicrobial/antiparasitic composition to the surface of the degradable, contaminatable and/or perishable substances; and or the incorporation of said antimicrobial/antiparasitic composition into said degradable, contaminatable and/or perishable substances;

said antimicrobial composition containing at least two GRAS (generally recognized as safe) flavoring agents;

(2) a preferred embodiment of the method as defined in (1) wherein said antimicrobial/antiparasitic composition contains one or more GRAS (generally recognized as safe) flavor alcohols or their derivatives (a) and one or more flavoring agents selected from polyphenol compounds (b) and GRAS flavor acids or their derivatives (c);

(3) another preferred embodiment of the method as defined in (1) wherein said antimicrobial/antiparasitic composition contains
  (i) at least one lipophilic GRAS (generally recognized as safe) flavoring agent; and
  (ii) at least one hydrophilic GRAS flavoring agent;

(4) a preferred embodiment of the method as defined in (1) to (3) wherein said antimicrobial/antiparasitic composition contains the GRAS flavor alcohol benzyl alcohol as a necessary component;

(5) a composition for the impregnation or surface treatment of microbially degradable, contaminatable and/or perishable substances/objects or parasite-attacked substances/objects (i.e., an impregnation agent) comprising an antimicrobial/antiparasitic composition as defined in (1) to (4);

(6) a composition for incorporation into microbiologically degradable, contaminatable and/or perishable substances/objects or into substances/objects prone to parasite attack comprising an antimicrobial/antiparasitic composition as defined in (1) to (4);

(7) the use of the composition as defined in (5) for the surface treatment of microbially degradable, contaminatable and/or perishable substances/objects or of parasite-attacked substances/objects or of substances/objects which have to be self-decontaminating; and (8) the use of an antimicrobial/antiparasitic composition as defined in (6) for incorporation into microbiologically degradable, contaminatable and/or perishable substances/objects, into substances/objects prone to parasite attack, or into substances/objects which have to be self-decontaminating.

The term "microbially degradable, contaminatable and/or perishable substances/objects" within the meaning of the present invention is to be understood to comprise the following natural and/or chemical materials:
  wood/timber and wood products including paper and wicker work;
  textiles and textile raw materials including leather and leather goods;
  plastic prone to germ contamination, including rubber;
  cosmetics and body care agents including hygiene and dressing products;
  natural and mineral insulation and sealant materials;
  construction materials made of mineral and natural substances;
  deodorants;
  insecticides and pesticides;
  filters;
  soils and fertilizers;
  animal-derived raw materials;
  paints and lacquers, lubricants, adhesives;
  detergents, cleaning agents and other hygiene products.

The term "impregnation, incorporation or surface treatment" when relating to the wood includes spraying directly after the felling of the trees, spraying during comminuting (sawing and shaping) by continuous addition to the comminuting machine, treatment of the comminuted material, e.g., during shipping, pressure impregnation of the processed product, and the long-term care by applying oils and paints. With wood pulps and papers, "impregnation" means the treatment of the product during processing, e.g., by addition during the preparation of such products, and an initial surface treatment during the installation of the equipment. In addition, for example, with air filters, the service life can also be further extended by a later surface treatment. Coatings of natural and/or chemical materials can be impregnated either by adding the impregnation agent during the preparation process or by a later surface treatment. In addition, "impregnation" within the meaning of the present invention may also mean the addition of the antimicrobial composition to paints and lacquers. Surface disinfection or impregnation is effected, in particular, by spraying, dipping, nebulizing, scouring and wiping, which may be with or without pressure, at room temperature or hot.

In the following, the substances which can be employed according to the invention, are further described in more detail:

The GRAS flavoring agents, GRAS flavor alcohols and GRAS flavor acids mentioned above in (1) to (4) are recognized by the FDA authority as commercially safe for use in foods (GRAS=generally recognized as safe in food). The mentioned GRAS flavoring agents are the compounds mentioned in the FEMA/FDA GRAS Flavour Substances Lists GRAS 3-15 Nos. 2001-3815 (as of 1997). This list contains natural and naturally occurring synthetic flavoring agents approved by the American public health authority, FDA, for use in foodstuffs: FDA Regulation 21 CFR 172.515 for naturally occurring synthetic flavoring agents (Synthetic Flavoring Substances and Adjuvants) and FDA Regulation 21 CFR 182.20 for natural flavoring agents (Natural Flavoring Substances and Adjuvants). Suitable GRAS flavoring agents according to the present invention include, for example, (a) GRAS flavor alcohols or their derivatives, (b) polyphenol compounds. (c) GRAS flavor acids or their derivatives, (d) phenols or their derivatives, (e) esters, (f) terpenes, (g) acetals, (h) aldehydes and (i) essential oils.

In detail, the following GRAS flavor alcohols (a) may be employed, for example:

benzyl alcohol, acetoin (acetylmethylcarbinol), ethyl alcohol (ethanol), propyl alcohol (1-propanol), isopropyl alcohol (2-propanol, isopropanol), propylene glycol, glycerol, n-butyl alcohol (n-propyl carbinol), iso-butyl alcohol (2-methyl-1-propanol), hexyl alcohol (hexanol), L-menthol, octyl alcohol (n-octanol), cinnamyl alcohol (3-phenyl-2-propene-1-ol), α-methylbenzyl alcohol (1-phenyl-ethanol), heptyl alcohol (heptanol), n-amyl alcohol (1-pentanol), iso-amyl alcohol (3-methyl-1-butanol), anisalcohol (4-methoxybenzyl alcohol, p-anisalcohol), citronellol, n-decyl alcohol (n-decanol), geraniol, β,γ-hexenol (3-hexenol), lauryl alcohol (dodecanol), linalool, nerolidol, nonadienol (2,6-nonadien-1-ol), nonyl alcohol (nonanol-1), rhodinol, terpineol, borneol, clineol (eucalyptol), anisole, cuminyl alcohol (cuminol), 10-undecene-1-ol, 1-hexadecanol. As derivatives, both natural and synthetic (naturally occurring or not) derivatives can be employed. Suitable derivatives include, for example, the esters, ethers and carbonates of the above mentioned GRAS flavor alcohols. Particularly preferred GRAS flavor alcohols are the aromatic GRAS flavor alcohols of the above list (benzyl alcohol being particularly preferred), 1-propanol, glycerol, propylene glycol, n-butyl alcohol, citronellol, hexanol, linalool, acetoin and their derivatives.

As component (b), the following polyphenols may be employed:

catechol, resorcinol, hydroquinone, phloroglucinol, pyrogallol, cyclohexane, resveratrol, usnic acid, acylpolyphenols, lignins, anthocyans, flavones, catechols, gallic acid derivatives (e.g., tannins, gallotannin, tannic acids, gallotannic acids), carnosol, carnosolic acid (including their derivatives, such as (2,5-dihydroxy-phenyl)carboxylic and (2,5-dihydroxyphenyl)alkylenecarboxylic substitutions, salts, esters, amides); caffeic acid and its esters and amides, flavonoids (e.g., flavone, flavonol, isoflavone, gossypetin, myricetin, robinetin, apigenin, morin, taxifolin, eriodictyol, naringin, rutin, hesperidin, troxerutin, chrysin, tangeritin, luteolin, catechols, quercetin, fisetin, kaempferol, galangin, rotenoids, aurones, flavonols, diols), extracts, e.g., from *Camellia, Primula*. Further, their possible derivatives, e.g., salts, acids, esters, oxides and ethers, may also be used. A particularly preferred polyphenol is tannin (a GRAS compound).

As component (c), the following GRAS acids may be used, for example: acetic acid, aconitic acid, adipic acid, formic acid, malic acid (1-hydroxysuccinic acid), capronic acid, hydrocinnamic acid (3-phenyl-1-propionic acid), pelargonic acid (nonanoic acid), lactic acid (2-hydroxypropionic acid), phenoxyacetic acid (glycolic acid phenyl ether), phenylacetic acid (α-toluenic acid), valeric acid (pentanoic acid), iso-valeric acid (3-methylbutyric acid), cinnamic acid (3-phenylpropenoic acid), citric acid, mandelic acid (hydroxyphenylacetic acid), tartaric acid (2,3-dihydroxybutanedioic acid; 2,3-dihydroxysuccinic acid), fumaric acid, tannic acid and their derivatives.

Suitable derivatives of the GRAS flavor acids according to the present invention are esters (e.g., $C_{1-6}$ alkyl esters and benzyl esters), amides (including N-substituted amides) and salts (alkali, alkaline earth and ammonium salts) of the above mentioned acids. According to the present invention, the term "derivatives" also encompasses modifications of the side-chain hydroxy functions (e.g., acyl and alkyl derivatives) and modifications of the double bonds (e.g., the perhydrogenated and hydroxylated derivatives of the mentioned acids).

As component (d), the following phenol compounds may be employed: thymol, methyleugenol, acetyleugenol, safrol, eugenol, isoeugenol, anethole, phenol, methylchavicol (estragol; 3-(4-methoxyphenyl)-1-propene), carvacrol, α-bisabolol, formesol, anisole (methoxybenzene), propenylguaethol (5-propenyl-2-ethoxyphenol) and their derivatives. Derivatives within the meaning of the present invention are compounds in which the phenolic hydroxy group is esterified or etherified.

As GRAS esters (component (e)), for example, allicin and the following acetates may be used: iso-amyl acetate(3-methyl-1-butyl acetate), benzyl acetate, benzylphenyl acetate, n-butyl acetate, cinnamyl acetate(3-phenylpropenyl acetate), citronellyl acetate, ethyl acetate(acetic ester), eugenol acetate(acetyleugenol), geranyl acetate, hexyl acetate(hexanyl ethanoate), hydrocinnamyl acetate(3-phenylpropyl acetate), linalyl acetate, octyl acetate, phenylethyl acetate, terpinyl acetate, triacetin (glyceryl triacetate), potassium acetate, sodium acetate and calcium acetate. Further suitable esters are the ester derivatives of the above defined acids (component (c)).

As terpenes (component (f)), there may be used, for example, camphor, limonene and β-caryophyllene.

The acetals (component (g)) which can be used include, e.g., acetal, acetaldehyde dibutyl acetal, acetaldehyde dipropyl acetal, acetaldehyde phenethyl propyl acetal, cinnamic aldehyde ethylene glycol acetal, decanal dimethyl acetal, heptanal dimethyl acetal, heptanal glyceryl acetal and benzaldehyde propylene glycol acetal.

As aldehydes (component (h)), there may be used, e.g., acetaldehyde, anisaldehyde, benzaldehyde, iso-butyl aldehyde (methyl-1-propanal), citral, citronellal, n-caprylic aldehyde (n-decanal), ethylvanillin, furfural, heliotropin (piperonal), heptyl aldehyde (heptanal), hexyl aldehyde (hexanal), 2-hexenal (β-propylacrolein), hydrocinnamic aldehyde (3-phenyl-1-propanal), lauryl aldehyde (dodecanal), nonyl aldehyde (n-nonanal), octyl aldehyde (n-octanal), phenylacetal-dehyde (1-oxo-2-phenylethane), propionaldehyde (propanal), vanillin, cinnamic aldehyde (3-phenylpropenal), perillaldehyde and cuminaldehyde.

The following essential oils and/or alcoholic or glycolic extracts or extracts obtained by $CO_2$ high-pressure processes from the mentioned plants (component (i)) can also be employed according to the invention:

(i1) oils or extracts having a high content of alcohols: melissa, coriander, *cardamon, eucalyptus;*

(i2) oils or extracts having a high content of aldehydes: *Eucalyptus citriodora,* cinnamon, lemon, lemon grass, melissa, citronella, lime, orange;

(i3) oils or extracts having a high content of phenols: *origanum,* thyme, rosemary, orange, clove, fennel, camphor, mandarin, anise, cascarilla, estragon and pimento;

(i4) oils or extracts having a high content of acetates: lavender;

(i5) oils or extracts having a high content of esters: mustards, onion, garlic;

(i6) oils or extracts having a high content of terpenes: pepper, bitter orange, caraway, dill, lemon, peppermint, nutmeg.

A preferred embodiment of the antimicrobial/antiparasitic composition (1) contains at least one GRAS flavor alcohol (a), especially benzyl alcohol. Preferred are those compositions which contain less than 50% by weight, preferably less than 30% by weight, more preferably less than 20% by weight, of ethanol, isopropanol or benzyl alcohol or a mixture of these substances.

In another preferred embodiment of the present invention, the antimicrobial/antiparasitic composition contains at least one hydrophilic alcoholic GRAS flavoring agent and/or one hydrophilic non-alcoholic GRAS flavoring agent. The proportion of hydrophilic alcoholic GRAS flavoring agents may be up to 99% by weight of the composition and is preferably from 30 to 98% by weight, more preferably from 80 to 95% by weight. The proportion of hydrophilic non-alcoholic GRAS flavoring agents in the insecticidal composition may be up to 90% by weight and is preferably from 0.1 to 50% by weight. Preferred are those compositions which further contain benzyl alcohol and/or a polyphenol compound (b1) in addition to the mentioned hydrophilic compounds.

Said hydrophilic alcoholic GRAS flavoring agents are monohydric or polyhydric alcohols having from 2 to 10, preferably from 2 to 7, carbon atoms. Particularly preferred compounds include 1-propanol, glycerol, propylene glycol and acetoin. Hydrophilic non-alcoholic GRAS flavoring agents are selected from organic acids having from 1 to 15 carbon atoms and physiologically acceptable salts thereof, hydrophilic acetates and hydrophilic aldehydes. Preferred organic acids include those which contain from 2 to 10 carbon atoms, especially acetic acid, aconitic acid, formic acid, malic acid, lactic acid, phenylacetic acid, citric acid, mandelic acid, tartaric acid, fumaric acid, tannic acid, hydrocinnamic acid and their physiologically acceptable salts. Said hydrophilic acetate is preferably selected from allicin, triacetin, potassium acetate, sodium acetate and calcium acetate, and said hydrophilic aldehyde is preferably selected from furfural, propionaldehyde and vanillin.

A further preferred antimicrobial/antiparasitic composition is the composition stated above under (2). This composition may contain:

from 0.1 to 99.9% by weight, preferably from 0.5 to 99% by weight, of component (a);

from 0 to 25% by weight, preferably from 0.01 to 10% by weight, of component (b); and from 0 to 70% by weight, preferably from 0.01 to 30% by weight, of component (c).

In this embodiment of the invention, component (a) contains one or more GRAS flavor alcohols. Preferred is the use of two or three GRAS flavor alcohols. The mixing ratio of component (a) to component (b) is preferably between 10,000:1 and 1:10,000, more preferably between 1000:1 and 1:1000, and still more preferably between 100:1 and 1:100.

In a particularly preferred embodiment of the method according to the invention, said antimicrobial/antiparasitic composition contains (a1) benzyl alcohol as a necessary component and optionally (a1) one or more further GRAS flavor alcohols or their derivatives; and (b) one or more polyphenol compounds; and/or (c) one or more GRAS acids or their derivatives.

Suitable amounts of components (a1), (a2), (b) and (c) in this case are:

from 0.1 to 99% by weight, preferably from 0.1 to 75% by weight, of benzyl alcohol;

from 0 to 99.8% by weight, preferably from 0.01 to 99% by weight, of component (a2);

from 0 to 25% by weight, preferably from 0.01 to 10% by weight, of component (b); and/or from 0 to 70% by weight, preferably from 0.01 to 30% by weight, of component (c).

In these compositions, particularly preferred are those which necessarily contain a polyphenol compound (b) and optionally contain one or more further GRAS acids (c).

A particularly preferred antimicrobial/antiparasitic composition may further contain the GRAS flavor agents (d) to (i) mentioned above.

The proportion of components (d) to (i) in the antimicrobial/antiparasitic composition is preferably equal to or smaller than 25% by weight, preferably within a range of from 0.001 to 9% by weight. Preferred among the further GRAS flavoring agents are the phenols (d) and the essential oils (i).

In the composition employed in embodiment (3) of the method according to the invention, the lipophilic GRAS flavoring agents are preferably selected from ($a_l$) lipophilic GRAS flavor alcohols or their derivatives, (b) polyphenol compounds, ($c_l$) lipophilic GRAS flavor acids or their derivatives, (d) phenols or their derivatives, ($e_l$) lipophilic esters, (f) terpenes, (g) acetals, ($h_l$) lipophilic aldehydes and (i) essential oils. The antimicrobial composition preferably contains two of the mentioned GRAS flavoring agents.

Suitable lipophilic GRAS flavor alcohols ($a_l$) among the above defined alcohols (a) include, in particular:

aromatic GRAS flavor alcohols, including benzyl alcohol, 2-phenylethanol, 1-phenylethanol, cinnamyl alcohol, hydrocinnamyl alcohol, 1-phenyl-1-propanol and anisalcohol, and aliphatic GRAS flavor alcohols, including n-butyl alcohol, iso-butyl alcohol, hexyl alcohol, L-menthol, octyl alcohol, heptyl alcohol, n-amyl alcohol, iso-amyl alcohol, anisalcohol, citronellol, n-decyl alcohol, geraniol, β,γ-hexenol, lauryl alcohol, linalool, nerolidol, nonadienol, nonyl alcohol, rhodinol, terpineol, borneol, clineol, anisole, cuminyl alcohol, 10-undecene-1-ol and 1-hexadecanol and their derivatives. The aromatic GRAS flavor alcohols, especially benzyl alcohol, are preferred.

According to the present invention, the hydrophilic GRAS flavoring agent is a hydrophilic alcoholic GRAS flavoring agent ($a_h$) or a hydrophilic non-alcoholic GRAS flavoring agent, wherein said hydrophilic alcoholic GRAS flavoring agent ($a_h$), as mentioned above, is preferably a monohydric or polyhydric alcohol having from 2 to 10, preferably from 2 to 7, carbon atoms, which is more preferably selected from acetoin, ethyl alcohol, propyl alcohol, iso-propyl alcohol, propylene glycol and glycerol. Said hydrophilic non-alcoholic GRAS flavoring agent is preferably a hydrophilic organic GRAS flavor acid ($c_h$) having from 1 to 15 carbon atoms or a physiological salt thereof, a hydrophilic acetate ($e_h$) or a hydrophilic aldehyde ($h_h$). Preferred hydrophilic organic acids ($c_h$) include those which contain from 2 to 10 carbon atoms, especially acetic acid, aconitic acid, formic acid, malic acid, lactic acid, phenylacetic acid, citric acid, mandelic acid, tartaric acid, fumaric acid, tannic acid, hydrocinnamic acid and their physiological salts. Said hydrophilic acetate ($e_h$) is preferably allicin, triacetin, potassium acetate, sodium acetate and calcium acetate. Said hydrophilic aldehyde ($h_h$) is preferably selected from furfural, propionaldehyde and vanillin.

The lipophilic polyphenol compound (b), phenols or their derivatives (d), terpenes (f), acetals (g) and essential oils (i) in the composition of method (3) are preferably the above defined compounds (b), (d), (f), (g) and (i). The lipophilic GRAS flavor acids or their derivatives ($c_l$), lipophilic esters ($e_l$) and lipophilic aldehydes include all specifically mentioned acids, esters and aldehydes, except for the compounds ($c_h$), ($e_h$) and ($h_h$) specifically mentioned above.

In a preferred embodiment of method (3), the antimicrobial/antiparasitic composition contains either:

(i) two lipophilic GRAS flavor alcohols ($a_l$), but no benzyl alcohol and no polyphenol compounds (b); or (ii) benzyl alcohol and/or a polyphenol compound (b), but no further GRAS flavor alcohols.

It is particularly preferred for the antimicrobial/antiparasitic composition to contain exclusively non-alcoholic hydrophilic GRAS flavoring agents, especially exclusively a hydrophilic GRAS flavor acid ($c_h$), and for the antimicrobial/antiparasitic composition to contain from 0.01 to 99% by weight, preferably from 0.1 to 90% by weight, of benzyl alcohol or polyphenol compounds (b) and from 0.01 to 50% by weight, preferably from 0.1 to 30% by weight, of hydrophilic non-alcoholic GRAS flavoring agents.

In a further preferred embodiment of method (1), the antimicrobial/antiparasitic composition contains:

(A) one or more GRAS flavor alcohols (a) or their derivatives; and (B) one or more flavoring agents selected from polyphenol compounds (b) and lipophilic GRAS flavor acids or their derivatives (c).

It is preferred for this composition to contain from 0.1 to 99% by weight, preferably from 0.5 to 99% by weight, of component (a), from 0 to 25% by weight, preferably from 0.01 to 10% by weight, of component (b), and from 0 to 70% by weight, preferably from 0.01 to 30% by weight, of component (c).

In addition, the antimicrobial/antiparasitic composition may contain further GRAS flavoring agents selected from (d) phenols or their derivatives, ($e_l$) lipophilic esters, (f) terpenes, (g) acetals, ($h_l$) lipophilic aldehydes and (i) essential oils.

It is further preferred for component (A) of the antimicrobial/antiparasitic composition to contain benzyl alcohol as a necessary component (a1) and additionally one or more further lipophilic GRAS flavor alcohols or their derivatives ($a_l$). Preferably, this antimicrobial composition contains:

from 0.1 to 99% by weight, preferably from 0.1 to 75% by weight, of benzyl alcohol;

from 0 to 99.8% by weight, preferably from 0.01 to 99% by weight, of component ($a_l$); and from 0 to 25% by weight, preferably from 0.01 to 10% by weight, of component (b);

from 0 to 70% by weight, preferably from 0.01 to 30% by weight, of component (c).

The composition employed may contain further lipophilic GRAS flavoring agents (d) to (i) as defined above, preferably from 0.001 to 25% by weight, more preferably from 0.01 to 9% by weight, of said further GRAS flavoring agents (d) to (i). Said further lipophilic GRAS flavoring agents more preferably include phenols (d) and/or essential oils (i).

In a further particularly preferred embodiment of method (3), component (A) of the antimicrobial/antiparasitic composition consists of two lipophilic GRAS flavor alcohols, and component (B) contains at least one polyphenol compound (b). Said polyphenol compound (b) is preferably tannin, particularly preferred being a composition which contains from 20 to 98% by weight of benzyl alcohol and from 0.01 to 10% by weight of tannin.

Particularly preferred according to the present invention are those antimicrobial/antiparasitic compositions in which antimicrobially/antiparasitically active component exclusively consists of GRAS flavoring agents, i.e., does not contain any "derivatives" of the GRAS flavoring agents. As an example of such a composition, there may be mentioned a mixture of benzyl alcohol, one or two of the above mentioned GRAS flavor alcohols (a2) and tannin. Such mixture preferably contains from 0.1 to 98% by weight of benzyl alcohol and from 0.01 to 10% by weight of tannin. Another example of a preferred composition is a mixture of 2 alcohols, a polyphenol (especially tannin) and an essential oil (especially a phenolic essential oil, component (i3)).

In addition to components (a) to (i), the antimicrobial/insecticidal compositions may additionally contain further compounds (j), such as alcohols (j1), emulsifiers (j2), stabilizers (j3), antioxidants (j4), preservatives (j5), solvents (j6), carriers (j7) etc.

The proportion of components (j) in the antimicrobial/antiparasitic composition may be up to 95% by weight, is preferably lower than 10% by weight, and is preferably within a range of from 0.1 to 5% by weight.

According to the invention, the alcohols (j1) are monohydric or polyhydric alcohols having from 2 to 10 carbon atoms, preferably from 2 to 7 carbon atoms, not including the GRAS alcohols (a). Preferably, such amounts of GRAS flavor alcohols (a) and further alcohols (j1) are employed that their mixing ratio is between 1000:1 and 1:1000, especially between 100:1 and 1:100, more preferably between 10:1 and 1:10.

It is particularly preferred in the method according to the present invention to use systems which exclusively consist of GRAS flavoring agents, especially when the treated products come into contact with foodstuffs, because this also prevents contamination of the foodstuffs with non-GRAS compounds. Further, it should be taken care that the antimicrobial composition is free of ethanol and isopropanol, or free of noxious doses of ethanol and isopropanol, since these substances can be inhaled by the persons who effect the impregnation. In addition, there may be a danger of explosion when these compounds are used.

Finally, the invention also relates to substances/objects/products which have been surface-treated by the method according to the invention or into which the anti-microbial/antiparasitic composition has been incorporated.

The method according to the invention can provide an effective protection against the microorganisms or parasites described in the following:

Molds: mildew species, rust fungi, leaf spot fungi, *Fusarium* species, *Aspergillus* species, *Penicillium* species, *Rhizoctonia, Peronaspora, Phytophtora, Botrytis cinerea, Rhizoctonia solani, Aspergillus ocraceus, Aspergillus niger, Clavosporium fusarium, Penicillium*.

Parasites: Lepidoptera (*Chilo suppressalic, Chaphalocrosis medinalis, Ostrina nubialis*), *Myzus persicae*, (jumping) insects, cigarette beetles, mites, plant lice, flies, moths.

Viruses: tomato mosaic virus, X virus, Y virus, rice stripe virus, TYM virus, Rhizomania, BNYVV.

Special fungi/parasites which can be suppressed by the method according to the invention are summarized in the following Table:

| Name | Former and English names | Significance |
|---|---|---|
| Amylostereum areolatum | Stereum areolatum | red streakiness |
| Antrodia vaillantii | Poria vaillantii Broad-spored white polypore | most frequent pore house fungus |
| Armillaria mellea | Honey mushroom | parasite |
| Aspergillus niger | Black mold, Black aspergillus | "black mold" |
| Aspergillus flavus | | aflatoxins |
| Aureobasidium pullulans | Pullularia pullulans | blue staining of paints |
| Bispora antennata | Bispora monilioides | "black streakiness" |
| Ceratocystis fagacearum | | oak wilt |
| Ceratocystis fimbriata f. platani | | plane canker stain |
| Chaetomium globosum | | soft rot, test fungus |
| Chlorociboria aeruginascens | Chlorosplenium aeruginascens, Green wood cup fungus | "green stain" |
| Cladosporium spp. | | blue stain on cut wood |
| Coniophora puteana | Coniophora cerebella Cellar fungus | test fungus EN 113 |
| Daedalea quercina | Lenzites quercina Thick-maze oak polypore | heart wood degradation of oaks |
| Discula pinicola phonectria parasitica | Endothia parasitica | chestnut blight |
| Fomes fomentarius | Polyporus fomentarius Tinder fungus | parasite |
| Gloeophyllum abietinum | Lenzites abietina | window wood destroyer |
| Gloeophyllum separium | Lenzites sepiaria Yellow-red gill polypore | |
| Gloeophyllum trabeum | Lenzites trabea | test fungus EN 113 |
| Heterobasidion annosum | Fomes annosus Root fomes | root and butt rot |
| Laetiporus sulphureus | Polyporus sulphureus Sulphur fungs | parasite |
| Lentinus lepideus | Train wrecker | Tar-oil resistance, EN 113 |
| Meripilus giganteus | Giant polypore | parasite of road trees |
| Nectria coccinea | | beech bark disease |
| Ophiostoma minus | Ceratocystis minor | blue stain |
| Ophiostoma piceae | Ceratocystis piceae | blue stain |
| Ophiostoma ulmi | Ceratocystis ulmi | Dutch elm disease |
| Paxiullus panuoides | | |
| Paecilomyces variotii | | mine timber destroyer |
| Penicillium spp. | penicillium mold | Soft rot |
| Phaeolus spadiceus | Phaeolus schweinitzii Velvet-top fungus | parasite |
| Phanerochaete chtysosporium | amorphous: Sporotrichum pulverulentum | lignin degradation |
| Phellinus igniarius | Fomes igniarius False tinder fungus | parasite |
| Phellinus pini | Trametes pini Ring scale fungus | parasite |
| Phlebiopsis gigantea | Phanerochaete gigantea | biological forest protection |
| Piptoporus betulinus | Polyporus betulinus Birch polypore | parasite |
| Polyporus squamosus | Scaly fungus | |
| Schizophyllum commune | Split gill fungus | parasite |
| Serpula lactymans | Merulius lacrymans Tear fungus, House fungus | "Genetics wood fungi" |
| Serpula himantioides | Merulius silvester | |
| Sparassis crispa | Cauliflower fungus | |
| Stereum sanguinolentum | bleeding fungus | parasite red heart rot, red streakiness |
| Trametes versicolor | Coriolus versicolor Turkey-tail fungus | simultaneous rot |
| Trichaptum abietinum | Hirschioporus abietinus | test fungus EN 113 red streakiness |
| Trichoderma viride | (green mold) | |
| Tyromyces placenta | Postia, Oligoporus placenta | cellulases test fungus EN 113 |
| Xylobolus frustulatus | Stereum frustulosum | "partridge wood" |

| Culture/object | pest/organism/purpose |
|---|---|
| softwood/hardwood | freely eating Lepidoptera caterpillars |
| hardwood | Browntail moth |
| softwood/hardwood | Gypsy moth |
| softwood/hardwood | Nun moth |
| softwood | Pine moth |

-continued

| Culture/object | pest/organism/purpose |
|---|---|
| softwood | *Zeiraphera rufimitrana* leaf roller |
| softwood | Large brown pine weevil |
| softwood/hardwood | wood-dwelling bark beetle |
| softwood/hardwood | bark-dwelling bark beetle |
| softwood | Apple rust mite |

In addition to the above defined antimicrobial composition, the composition for impregnation according to the invention may also contain colorants, such as dyes and pigments, dispersants, solvents, hardeners, natural wood-protection biocides. Such natural wood-protection biocides and their preferred maximum content in the compositions according to the invention are shown in the following Table:

| Biocides employed | max. content in % |
|---|---|
| beech tar oil | 29 |
| oak bark | 1.0 |
| spruce distillate | — |
| galanga root | 1.0 |
| guaiac wood | 1.0 |
| wood vinegar | 10 |
| softwood tar | 12.0 |
| neem bark | — |
| clove oil | — |
| oreganum | 1.0 |
| juniper wood | 1.0 |
| winter green oil | |

The proportion of the antimicrobial/antiparasitic composition in the composition for impregnation, surface treatment or incorporation is from 0.001 to 99% by weight, preferably from 0.1 to 10% by weight.

An antimicrobial effect can be observed when the content of the antimicrobial/antiparasitic composition is from 0.001 to 100 mg/g, preferably from 0.1 to 50 mg/g (for incorporation or impregnation), or from 0.1 to 50 g/m$^2$ (for surface treatment) of treated substrate.

Thus, the present invention provides a treatment method which is safe in terms of health and ecologically acceptable, and which can be adapted to the respective microbially degradable, contaminated and/or perishable product. Further preferred antimicrobial/antiparasitic compositions are mentioned in WO 96/29895 and WO 98/58540, the disclosure of which is included herein by reference.

The present invention will be further illustrated by the following Examples.

EXAMPLES

The product protecting agents (PPAs) contain the following components (in % by weight);

PPA I:

10.0% polyphenol (here: tannin)

18.2% benzyl alcohol 60.0% propylene glycol 8.0% lactic acid 3.8% essential oil (here: a phenol-containing essential oil)

PPA II:

| benzyl alcohol | 50% | a1 |
|---|---|---|
| cinnamic aldehyde | 50% | g |

PPA III:

| benzyl alcohol | 50% | a1 |
|---|---|---|
| propylene glycol | 50% | b1 |

PPA IV:

| | | | |
|---|---|---|---|
| a) benzyl alcohol | 50% | a1 | |
| polyphenol (tannin) | 50% | b1 | |
| b) benzyl alcohol | 50% | a1 | |
| polyphenol (tannin) | 25% | b1 | |
| lactic acid | 25% | b2 | |
| c) benzyl alcohol | 25% | a1 | |
| propylene glycol | 50% | a2 | |
| polyphenol (tannin) | 25% | b1 | |
| d) benzyl alcohol | 25% | a1 | |
| propylene glycol | 25% | a2 | |
| polyphenol (tannin) | 25% | b1 | |
| lactic acid | 25% | b2 | |

PPA V:

| | | |
|---|---|---|
| a) propylene glycol | 25% | a2 |
| glycerol | 25% | a2 |
| lactic acid | 25% | b2 |
| tannin | 25% | b1 |
| b) propylene glycol | 50% | a2 |
| glycerol | 25% | b2 |
| lactic acid | 25% | b2 |
| c) propylene glycol | 50% | a2 |
| glycerol | 25% | b2 |
| tannin | 25% | b1 |

Example 1

Surface Self-Decontamination

Application: treatment of working surfaces, conveying belts, etc.

Food product: e.g., meat

Problem: germ increase due to growing biomass

Dosage: spray on surfaces in neat form

Performance (On Stainless Steel Working Desk)

1. Clean and disinfect working surface (with alcohol 70%)

2. Spray on PPA I and squeegee

3. Contaminate with Raw Meat

4. Spray on PPA I and squeegee

5. Take sample.

This process is performed in five periods with intervals of 15 min.

Bacteriology: The following germs/groups of germs are isolated or differentiated by official examination methods according to Section 35 LMBG (German Food and Consumer Goods Act): Total germ count, Enterobacteriaceae, lactobacilli.

Sampling: between the treatment periods.

Evaluation

Test object: $V_2A$ steel surface which was contaminated with a neck chop at regular intervals;

Control: before start of experiment: cleaning of the table and disinfection with 70% alcohol;

$V_2A$ steel surface was wiped with a neck chop at 15 min intervals to build up a biomass. From the $2^{nd}$ interval, the meat was sprayed with water;

PPA: spraying of the test surface with PPA I after cleaning and disinfection, wipe off with squeegee;

After contamination with the neck chop, the surface was sprayed with PPA and squeegeed, followed by taking the sample;

Immediately thereafter, the surface was recontaminated and squeegeed;

Test method: a surface area of 100 cm² was covered by means of a smear;

Results: see below

Comments: in combination with the application technique, PPA I is capable of reducing the total germ count by $10^5$, Enterobacteriaceae by $10^2$ and lactobacilli by $10^5$ on contaminated surfaces, i.e., a reduction factor of 5 for total germ count and lactobacilli.

Examination Results

|  | total germ count/smear | Enterobacteriaceae/smear | lactobacilli/smear |
|---|---|---|---|
| 1st contamination without squeegeeing | $6.7 \times 10^4$ | 20 | $6.6 \times 10^4$ |
| 6th contamination after squeegeeing | $2.3 \times 10^3$ | — | $2.3 \times 10^3$ |
| control without PPA I | $3.9 \times 10^5$ | $5.5 \times 10^2$ | $3.8 \times 10^5$ |
| immediately | $6.1 \times 10^3$ | — | $5.3 \times 10^3$ |
| after 15 minutes | $7.4 \times 10^3$ | — | $4.3 \times 10^3$ |
|  | $1.43 \times 10^4$ | — | $1.36 \times 10^4$ |
| after 30 minutes | $3.2 \times 10^3$ | — | $2.1 \times 10^3$ |
|  | $1.29 \times 10^4$ | 10 | $1.09 \times 10^4$ |
| after 45 minutes | $6.4 \times 10^3$ | — | $3.8 \times 10^3$ |
|  | $8.1 \times 10^3$ | — | $6.8 \times 10^3$ |
| after 60 minutes | $7.8 \times 10^3$ | — | $6.1 \times 10^3$ |
|  | $3.6 \times 10^4$ | 50 | $3.6 \times 10^4$ |
| after 75 minutes | $7.6 \times 10^3$ | — | $7.4 \times 10^3$ |
|  | $1.93 \times 10^4$ | — | $1.82 \times 10^4$ |
| after 90 minutes | $5.8 \times 10^3$ | — | $5.3 \times 10^3$ |
|  | $1.25 \times 10^4$ | — | $1.14 \times 10^4$ |
| control with PPA | 10 | — | — |
| immediately |  |  |  |
| after 15 minutes | — | — | — |
|  | — | — | — |
| after 30 minutes | — | — | — |
|  | — | — | — |
| after 45 minutes | — | — | — |
|  | — | — | — |
| after 60 minutes | — | — | — |
|  | — | — | — |
| after 75 minutes | — | — | — |
|  | — | — | — |
| after 90 minutes | — | — | — |
|  | — | — | — |

Example 2

Quantitative Suspension Experiment According to DVG (German Veterinary Association) Regulations Product PPA I Efficiency test: impregnation, surface treatment, incorporation, decontamination, self-decontamination, e.g., deodorant, paints, lacquers, lubricants, detergents, hygienic agents

| Test strain (cfu/ml) | conc. in volume % | time of action 60 min | control | log RF |
|---|---|---|---|---|
| E. coli ($1.1 \times 10^9$) | 8 | 0 | 980,000 |  |
|  |  | 0 |  |  |
|  |  | 0 | 980,000 | >4.99 |
|  | 10 | 0 | 980,000 |  |
|  |  | 0 |  |  |
|  |  | 0 | 980,000 | >4.99 |
|  | 12 | 0 | 980,000 |  |
|  |  | 0 |  |  |
|  |  | 0 | 980,000 | >4.99 |
| Pa. fluorescens ($1.7 \times 10^9$) | 8 | 0 | 2,800,000 |  |
|  |  | 0 |  |  |
|  |  | 0 | 2,800,000 | >5.45 |
|  | 10 | 0 | 2,800,000 |  |
|  |  | 0 |  |  |
|  |  | 0 | 2,800,000 | >5.45 |
|  | 12 | 0 | 2,800,000 |  |
|  |  | 0 |  |  |
|  |  | 0 | 2,800,000 | >5.45 |
| Staph. aureus ($2.9 \times 10^9$) | 8 | 0 | 1,250,000 |  |
|  |  | 0 |  |  |
|  |  | 0 | 1,250,000 | >5.10 |
|  | 10 | 0 | 1,250,000 |  |
|  |  | 0 |  |  |
|  |  | 0 | 1,250,000 | >5.10 |
|  | 12 | 0 | 1,250,000 |  |
|  |  | 0 |  |  |
|  |  | 0 | 1,250,000 | >5.10 |
| Salm. enteritidis ($1.7 \times 10^9$) | 8 | 0 | 1,600,000 |  |
|  |  | 0 |  |  |
|  |  | 0 | 1,600,000 | >5.20 |
|  | 10 | 0 | 1,600,000 |  |
|  |  | 0 |  |  |
|  |  | 0 | 1,600,000 | >5.20 |
|  | 12 | 0 | 1,600,000 |  |
|  |  | 0 |  |  |
|  |  | 0 | 1,600,000 | >5.20 |
| List. monocytogenes ($1.5 \times 10^9$) | 8 | 0 | 2,050,000 |  |
|  |  | 0 |  |  |
|  |  | 0 | 2,050,000 | >5.31 |
|  | 10 | 0 | 2,050,000 |  |
|  |  | 0 |  |  |
|  |  | 0 | 2,050,000 | >5.31 |
|  | 12 | 0 | 2,050,000 |  |
|  |  | 0 |  |  |
|  |  | 0 | 2,050,000 | >5.31 |
| Lactob. brevis ($9.3 \times 10^8$) | 8 | 1.540 | 1,140,000 |  |
|  |  | 1.760 |  |  |
|  |  | 1.650 | 1,140,000 | >2.84 |
|  | 10 | 0 | 1,140,000 |  |
|  |  | 0 |  |  |
|  |  | 0 | 1,140,000 | >5.06 |
|  | 12 | 0 | 1,140,000 |  |
|  |  | 0 |  |  |
|  |  | 0 | 1,140,000 | >5.06 |
| Ent. serogenes ($7.0 \times 10^7$) | 8 | 0 | 26,500 |  |
|  |  | 0 |  |  |
|  |  | 0 | 26,500 | >3.42 |
|  | 10 | 0 | 26,500 |  |
|  |  | 0 |  |  |
|  |  | 0 | 26,500 | >3.42 |
|  | 12 | 0 | 26,500 |  |
|  |  | 0 |  |  |
|  |  | 0 | 26,500 | >3.42 |

Example 3

Product Protection of Wood with Superposed Cheese (Provocation Test)

Product PPA I—Surface Treatment and Impregnation of Wood

|  | un-treated | treated sprayed with PPA I (concentration) | treated soaked with PPA I (concentration) | start mold growth between cheese and wooden board | start mold growth only on wooden board | atmospheric humidity/ temperature |
|---|---|---|---|---|---|---|
| spruce glue wood | X |  |  | 8th day after treatment | 19th day after treatment | 85%/15° C. |
| spruce glue wood |  | X (12.7 g/m²) |  | — | — | 85%/15° C. |
| spruce glue wood |  |  | X 60 g/m² | — | — | 85%/15° C. |
| spruce solid wood | X |  |  | 11th day after treatment | 20th day after treatment | 85%/15° C. |
| spruce solid wood |  | X (18.5 g/m²) |  | — | — | 85%/15° C. |
| spruce solid wood |  |  | 185 g/m² | — | — | 85%/15° C. |
| bankirai | X |  |  | 6th day after treatment | 11th day after treatment | 85%/15° C. |
| bankirai* |  | X (5.1 g/m²) |  | — | — | 85%/15° C. |

*a tropic wood
All wooden boards treated with PPA had not exhibited any growth of mold by the 35th day after treatment.
Thereafter, the experiment was discontinued (end of cheese maturing).

Example 4A

Product Protection of Wood with Superposed Cheese (Provocation Test)

Product PPA II and III—Surface Treatment of Wood as a Function of PPA II and III Concentrations

|  | un-treated | treated sprayed with PPA I concentration) 100 | treated sprayed with PPA I concentration) 50 | treated soaked with PPA I (concentration) | atmospheric humidity/ temperature |
|---|---|---|---|---|---|
| spruce glue wood | $X^8$ | — | $X^{11}$ | — | 85%/15° C. |
|  |  |  |  | $X^{12}$ |  |
| spruce solid wood | $X^{11}$ | — | $X^{13}$ | — | 85%/15° C. |
|  |  |  |  | $X^{18}$ |  |
| bankirai* | $X^{11}$ | — | $X^{15}$ | — | 85%/15° C. |
|  |  |  |  | $X^{14}$ |  |

*a tropic wood
X: Mold growth positive (index indicates on which day mold growth between the cheese and wooden board occurred);
—: Mold growth negative, no mold growth had occurred by the 35th day after the treatment. Thereafter, the experiment was discontinued (end of cheese maturing).

Dosage PPA:

spruce glue wood 100: 15 g/m² of PPA II or III//50: 7.5 g/m² of PPA II or III
spruce solid 100: 20 g/m² of PPA II or III//50: 10 g/m² of PPA II or III
bankirai 100:5 g/m² of PPA II or III//50: 2.5 g/m² of PPA II or III

Example 4B

Product Protection of Wood with Superposed Cheese (Provocation Test)

Product PPA IV—Surface Treatment of Wood

|  | untreated | a 100 | a 50 | b 100 | b 50 | c 100 | c 50 | d 100 | d 50 | atmospheric humidity/ temperature |
|---|---|---|---|---|---|---|---|---|---|---|
| spruce glue wood | $X^8$ | — | — | — | — | — | — | — | — | 85%/15° C. |

(treated mold growth PPA IV)

-continued

| | untreated | treated mold growth PPA IV | | | | | | | atmospheric humidity/ temperature |
|---|---|---|---|---|---|---|---|---|---|
| | | a 100 | a 50 | b 100 | b 50 | c 100 | c 50 | d 100 | d 50 | |
| spruce solid wood | $X^{11}$ | — | — | — | — | — | — | — | — | 85%/15° C. |
| bankirai* | $X^{11}$ | — | — | — | — | — | — | — | — | 85%/15° C. |

*a tropic wood
X: Mold growth positive (index indicates on which day mold growth between the cheese and wooden board occurred);
—: Mold growth negative, no mold growth had occurred by the 35$^{th}$ day after the treatment. Thereafter, the experiment was discontinued (end of cheese maturing).

Dosage PPA IV:

| spruce glue wood | 100: 15 g/m$^2$ of IVa, b, c or d//50: 7.5 g/m$^2$ of IVa, b, c or d |
|---|---|
| spruce solid wood | 100: 20 g/m$^2$ of IVa, b, c or d//50: 10 g/m$^2$ of IVa, b, c or d |
| bankirai | 100: 5 g/m$^2$ of IVa, b, c or d//50: 2.5 g/m$^2$ of IVa, b, c or d |

Example 4C

Product Protection of Wood with Superposed Cheese (Provocation Test)

Product PPA V—Surface Treatment of Wood

| | un- treat- ed | treated mold growth PPA V | | | | | | atmos- pheric humidity/ temper- ature |
|---|---|---|---|---|---|---|---|---|
| | | a 100 | a 50 | b 100 | b 50 | c 100 | c 50 | |
| spruce glue wood | $X^8$ | — | $X^{20}$ | — | $X^{10}$ | — | $X^{14}$ | 85%/15° C. |
| spruce wood | $X^{11}$ | — | $X^{20}$ | — | $X^{10}$ | — | $X^{14}$ | 85%/15° C. |
| bankirai* | $X^{11}$ | — | $X^{20}$ | — | $X^{10}$ | — | $X^{14}$ | 85%/15° C. |

*a tropic wood
X: Mold growth positive (index indicates on which day mold growth between the cheese and wooden board occurred);
—: Mold growth negative, no mold growth had occurred by the 35$^{th}$ day after the treatment. Thereafter the experiment was discontinued (end of cheese maturing).

Dosage PPA V:

| spruce glue wood | 100: 15 g/m$^2$ of Va, b or c//50: 7.5 g/m$^2$ of Va, b or c |
|---|---|
| spruce solid wood | 100: 20 g/m$^2$ of Va, b or c//50: 10 g/m$^2$ of Va, b or c |
| bankirai | 100: 5 g/m$^2$ of Va, b or c//50: 2.5 g/m$^2$ of Va, b or c |

Example 5

Prevention of Mold Growth by Coating Illustrated for Cheese Maturing

Application: added to cheese cover agent

Food product: sliceable cheese

Problem: mold growth during cheese maturing

Dosage: 2% by weight ad coating (PPA I)

No. of samples: 10×30 g each of O samples and - samples

Performance

Simulation in a Climatic Room for Cheese Maturing

Temperature: 15° C., rel. humidity about 75%

Treatment of 8 loaves of raw cheese each with neutral or PPA I coating

The loaves are turned over every day.

Object/result: Reduction of mold growth as compared to O sample during maturing

Visual check: Mold and yeasts on the cheese surface

Sampling: Visual check for appearance, daily.

Evaluation

Off-storage results in climatic room K 43: 15° C., 75% rel. humidity

Storage of the sliceable goat cheese: July 15, taken from the saline bath

Coating: On July 28 on one side
  On August 29 on the opposite side followed by daily turning over and checking.

Test for Mold Loading of K 34 Using RCS Device:

| on July 21 | 210/m$^3$ |
|---|---|
| on July 24 | 65/m$^3$ |

Results of Serial Experiment: Visual Check for Molds

| checking day | n = 8, no PPA | n = 8, with PPA |
|---|---|---|
| August 9 | 1 | 0 |
| August 10 | 4 | 0 | n = number of cheese loaves

Comments: The untreated and treated cheese loaves (PPA I in coating) were matured under the conditions possible in a climatic room (see test for mold loading). In contrast to the PPA I samples, the O samples exhibited visual mold growth from the 12$^{th}$ maturing day.

PPA I Surface Treatment—Service Lives

| Filter | PPA spraying agent | Dosage | Molds Section 35 LMBG* | Bacteria Section 35 LMBG* |
|---|---|---|---|---|
| F-0 | O sample | 0 | $8 \times 10^5/25\ cm^2$ | $10^4/25\ cm^2$ |
| F-1 | | 0.1 g/m² | $7 \times 10^3/25\ cm^2$ | $8 \times 10^1/25\ cm^2$ |
| F-2 | | 1 g/m² | $2 \times 10^2/25\ cm^2$ | <10 |
| F-3 | | 10 g/m² | $<10/25\ cm^2$ | <10 |

*LMBG = German Food and Consumer Goods Act

What is claimed is:

1. A method for the impregnation and treatment of wood comprising the step of
    applying a non-toxic composition to the wood
    wherein said composition consists essentially of benzyl alcohol, tannic acid, tannin and lactic acid.

2. A method for the impregnation and treatment of wood comprising the step of applying a non-toxic composition to the wood, wherein
    the composition consists essentially of benzyl alcohol, tannic acid, tannin lactic acid and essential oils.

3. A method for the impregnation and treatment of wood comprising the step of applying a composition to the wood, wherein said composition consists essentially of benzyl alcohol, tannic acid, tannin lactic acid and glycerol.

4. The method according to claim 3, wherein said composition comprises less than 50% by weight of benzyl alcohol.

5. The method for the impregnation and treatment of wood according to claim 1 comprising the step of applying a non-toxic composition to the wood, wherein said composition comprises from 0.1 to 98% by weight of benzyl alcohol and from 0.01 to 25% by weight of tannin.

6. The method according to claim 1, wherein said composition consists essentially of:
    from 0.01 to 99% by weight of benzyl alcohol and
    from 0.01 to 50% by weight of tannic acid.

7. A method for the impregnation and treatment of wood comprising the step of applying a composition to the wood, wherein said composition consists essentially of benzyl alcohol (a), propyl alcohol (b), tannin (c), tannic acid (d) and lactic acid (e).

8. The method according to claim 1, wherein said composition consists essentially of:
    from 0.1 to 99% by weight of benzyl alcohol;
    from 0.01 to 25% by weight of tannin;
    from 0.01 to 70% by weight of tannic acid and lactic acid.

9. A method for the impregnation and treatment of wood comprising the step of applying a non-toxic composition to the wood, wherein said composition comprises benzyl alcohol, propylene glycol, tannin, tannic acid and lactic acid.

10. The method of treatment of wood comprising the step of applying the composition as defined in claim 1 by spraying.

11. A method for the impregnation and treatment of wood comprising the step of applying a non-toxic composition to the wood, wherein said composition comprises:
    (i) benzyl alcohol;
    (ii) propylene glycol;
    (iii) tannic acid;
    (iv) tannin;
    (v) lactic acid and
    (vi) essential oils or extracts selected from *Eucalyptus citriodora*, cinnamon lemon, lemon grass, melissa, citronella lime and orange.

12. A method for the impregnation and treatment of wood comprising the step of applying a non-toxic composition to the wood, wherein said composition consists essentially of benzyl alcohol, tannic acid, tannin, lactic acid and lavender.

13. A method for the impregnation and treatment of wood comprising the step of applying a non-toxic composition to the wood, wherein said composition comprises benzyl alcohol, tannic acid, propylene glycol, tannin, lactic acid and essential oils having a high content of alcohols, melissa, coriander, *cardamon* and *eucalyptus*.

14. A method for the impregnation and treatment of wood comprising the step of applying a non-toxic composition to the wood, wherein said composition comprises benzyl alcohol, propylene glycol, tannic acid, tannin, lactic acid, and essential oils selected from pepper, bitter orange, caraway, dill, lemon, peppermint, and nutmeg.

15. A method for the impregnation and treatment of wood comprising the step of applying a composition to the wood wherein said composition consists essentially of benzyl alcohol, tannic acid, propylene glycol, lactic acid and cinnamyl alcohol.

16. A method of treatment of wood comprising the step of incorporating the composition as defined in claim 15 by spraying.

17. A method for the impregnation and treatment of wood comprising the step of applying a composition to the wood, wherein said composition comprises:
    from 0.1 to 99% by weight of benzyl alcohol;
    from 0.01 to 99.8% by weight of propylene glycol;
    from 0.01 to 25% by weight of tannin;
    from 0.01 to 70% by weight of tannic acid and
    from 0.01 to 30% weight of lactic acid.

18. The method for the impregnation and treatment of wood according to claim 17 comprising the step of applying a non-toxic composition to the wood, wherein said composition comprises from 20 to 98% by weight of benzyl alcohol and from 0.01 to 10% by weight of tannin.

* * * * *